United States Patent [19]
Shah

[11] Patent Number: 6,010,535
[45] Date of Patent: Jan. 4, 2000

[54] JOINT REPLACEMENT SYSTEM

[76] Inventor: Mrugesh K. Shah, 403 Trailscourt, Houston, Tex. 77024

[21] Appl. No.: 09/070,205

[22] Filed: Apr. 30, 1998

[51] Int. Cl.⁷ .................................................. A61F 2/32
[52] U.S. Cl. ................................................................ 623/22
[58] Field of Search ............................... 623/18, 22, 23, 623/19, 21

[56] References Cited

U.S. PATENT DOCUMENTS

| | | | |
|---|---|---|---|
| 2,947,308 | 8/1960 | Gorman | 623/23 |
| 3,543,749 | 12/1970 | Grove | 623/23 |
| 3,843,975 | 10/1974 | Tronzo | 623/23 |
| 4,206,517 | 6/1980 | Pappas et al. | 623/18 |
| 4,783,192 | 11/1988 | Wroblewski et al. | 623/23 |
| 4,840,632 | 6/1989 | Kampner | 623/18 |
| 4,846,840 | 7/1989 | Leclercq et al. | 623/18 |
| 4,895,572 | 1/1990 | Chernoff | 623/23 |
| 5,376,125 | 12/1994 | Winkler | 623/23 |

FOREIGN PATENT DOCUMENTS

| | | | |
|---|---|---|---|
| 634153 | 1/1995 | European Pat. Off. | 623/22 |
| 2845231 | 5/1979 | Germany | 623/22 |
| 1708329 | 1/1992 | U.S.S.R. | 623/18 |

*Primary Examiner*—Jeffrey A. Smith
*Assistant Examiner*—Eduardo C. Robert
*Attorney, Agent, or Firm*—Harrison & Egbert

[57] ABSTRACT

A replacement system for a joint including a first cup member having an interior lining material and forming a hemispherical cavity therein, a ball member received within the hemispherical cavity and being cantable within the cavity, a securing member connected to the first cup member for affixing the first cup member within an acetabulum area of the pelvic bone of a human joint, and an affixing member interconnected to the ball member for affixing the ball member against the femoral head area of the femur of a human joint. The ball has an outer diameter of no more than one inch. The securing member is a screw having one end embedded into the first cup member and extending through the pelvic bone. The affixing member is a shaft connected at one end to the ball member and extends into the femur bone. The affixing member further includes a nail extending through a portion of the femur and engaged with the shaft distal the ball member. This nail is secured to the femur through the use of surgical screws.

17 Claims, 4 Drawing Sheets

JOINT REPLACEMENT SYSTEM

TECHNICAL FIELD

The present invention relates to various medical devices used for the replacement of human joints. More particularly, the present invention relates to methods and apparatus for replacing human joints, in particular, hip joints.

BACKGROUND ART

Prostheses for the replacement of hip joints are already known. Originally, only the ball-end on the head of the femur could be replaced, but it has since proved possible to replace either part of the hip joint, that is to say, the acetabulum or the ball-end on the head of the femur.

The number of those living with hip prostheses is increasing more and more at the present time. The number of implanted artificial hip joints is estimated to be two thousand per day. The further increase of the cases into the millions is accounted for by the fact that the diseases of the hip joints due to wear are increasing numerically along with the rapid rise of the age of the population accompanied by a corresponding development of the medical technique.

Existing techniques for the carrying out of the hip replacement operation are extremely invasive. As such, the patient will require long periods of rehabilitation and long periods of hospital stay. Since a great deal of biological material is removed or replaced in the patient, a great amount of time is required for healing. Furthermore, the operative procedures are very time-consuming and very expensive.

Existing hip replacement techniques initially require the exposure of the femur. The hip must be dislocated so that the level of the neck resection can be measured proximally from the lesser femoral head based on the preoperatively templated measurement. In addition, the center of the femoral head is approximated and marked. A right angle retractor is used to judge the anatomical relationship for the later restoration of leg length and offset. The femoral neck cut is made by using a femoral broach as a template, by using the femoral neck cutting guide, or by using a femoral resection template. The neck cut is made slightly horizontal, which allows the use of the calcar planer to obtain a smooth surface for eventual flush collar-calcar seating.

Following the removal of the femoral head, a partial superior and anterior capsulectomy is performed to allow exposure of the anterior acetabular rim. Hohmann or similar retractors are placed over the anterior rim for retraction of the shaft anteriorly. Posterior and superior Charnley pin retractors are placed in the interval between the capsule and the labrum to allow complete exposure. The acetabular rim is then completely exposed by thorough removal of the acetabular labrum.

Once acetabular exposure has been accomplished, reaming is initiated. Reaming continues until concentric removal of all remaining acetabular cartilage and the exposure of punctate bleeding in the subchondral plate is achieved. The medial landmark for correct depth is the acetabular floor visualized through the acetabular fossa. A cup sizer corresponding to the last reamer used is placed on a handle and inserted into the acetabulum. The acetabular cup sizers are the same size as the actual implant and should fit snugly into the acetabulum.

It is then necessary to insert the cup. To correctly judge the appropriate component position, a down-sized acetabular sizer can be easily inserted and positioned into the acetabulum so as to allow removal of any overhanging anterior, posterior or superior osteophytes. Once these steps have been completed, the correct acetabular shell is locked into the acetabular positioner and driven into a fully seated position. Screws can then be used for supplemental fixation.

After the placement of the acetabular component, attention is then turned to the femur. The femoral canal is identified with a hand-held reamer. Power reaming is initiated with a conical reamer. The reamer is advanced slowly within the canal until the proximal cutting edge is at the level of the calcar. As the reamer is withdrawn, lateral pressure is exerted to insure proper lateralization within the canal. Reaming proceeds in one millimeter or two millimeter increments depending on the bone density. Once the appropriate conical reamer has been passed, rasping is initiated. The rasp should be oriented so that the mediolateral axis of the rasp is parallel to the anatomic mediolateral axis of the femoral neck. The rasp is impacted until it is slightly below the level of the initial calcar cut. Subsequently, larger rasps are used until the final rasping is completed with the appropriate size. With the proper size rasp in place, the calcar is planed flush by using the calcar trimmer. With the final rasp still in place, provisional heads/necks are selected to determine the appropriate neck length in order to restore the lateral offset. Trial reduction is carried out to assure that proper leg length and stability are achieved. The stem corresponding to the size of the final rasp used is threaded onto the stem inserter/extractor and impacted into a fully seated position. The collar should seat flush against the medial calcar and the lateral shoulder should seat against the femoral head. After filly seating the femoral component, the appropriate modular head is impacted into the femoral neck. The hip is now ready to be reduced.

As can be seen, this procedure is quite invasive. A great deal of manipulation is required by the surgeon so as to properly install the artificial hip. Under certain circumstances, the patient does not fully recover from such invasive surgery. A great deal of rehabilitation and recovery are required to filly recover from such an invasive operation. As such, a need has developed so as to carry out a less invasive technique for the installation of a hip replacement.

In the past, various patents have issued relating to hip replacement operations and to hip prostheses.

U.S. Pat. No. 3,748,662, issued on Jul. 31, 1973 to A. J. Helfet, describes a surgical procedure for replacing the natural components of a bicondylar joint in a human limb. The prosthetic implant has two pairs of coacting male and female condylar components. The male and female components which replace the natural lateral condyles are spherical or spheroidal in shape to simulate a ball and sock joint. Both male components and both female components can be formed on respective rigid carriers or they may optionally be separate for individual fixation to the patient's limb.

U.S. Pat. No. 3,894,297, issued on Jul. 15, 1975 to Mittelmeier et al., describes a hip joint prosthesis which comprises a substantially frustoconical acetabulum member provided with supporting ribs in the form of a tapering thread and a prosthesis shaft provided with circular supporting ribs allowing anchorage of the prosthesis and the acetabulum member without using a cement or other adhesive.

U.S. Pat. No. 4,187,559, issued on Feb. 12, 1980 to Grell et al., describes a body joint endoprosthesis including an anchoring member having a shaft anchored in a first bone and a pivot member connected to the anchoring member by a pivot joint. The pivot member includes a first body joint member and a support element that bears against a seating surface of the first bone. The first body joint member and the second body joint member are connected to the second bone so as to form the body implant joint.

U.S. Pat. No. 4,355,427, issued on Oct. 26, 1982 to W. Schneider, describes an artificial humerus head having a groove in its exterior surface for receiving the long biceps tendon. A cover bridges the groove to form an elongated open-end channel for the tendon and makes it possible to arrange the long biceps tendon in the channel without separation thereof from the head.

U.S. Pat. No. 4,530,115, issued on Jul. 23, 1985 to Muller et al., describes a shank for a prosthesis which is composed of a blade which carries a joint head and a wedge-shaped end piece. The end piece is driven in along a guide in the lateral narrow side of the blade while the blade remains in a fixed position. The wedge-shaped form of the end piece permits fixation of the blade at a predetermined height such that the joint head can be at the level of the trochanter tip.

U.S. Pat. No. 4,775,381, issued on Oct. 4, 1988 to Tari et al., describes a hip prosthesis formed with a conventional head provided with a spherical shape, a neck, and a stem. A guide profile is formed along the outer straight side of the stem and contains components which are parallel with the side. The guide profile fits the inner surface of the medullary cavity nail so as to allow the simultaneous use of the hip prosthesis and the medullary cavity nail and the nailing of the already prosthetized femur.

U.S. Pat. No. 5,026,399, issued on Jun. 25, 1991 to Engelbrecht et al., describes a prosthetic device for the partial or total replacement of a bone, such as a femur. The prosthesis has a rod-like bridging member which spans the major part of the gap between the two joints. An abutment member is mounted at either end of the bridging member and each of the abutment members engages a bone adjacent that which is to be partially or totally replaced. Each of the abutment members may constitute part of an artificial joint. The abutment members may be rotatable relative to one another and to the bridging member about the longitudinal axis of the latter in order that the abutment members may assume a relative angular orientation best suited to the characteristics of the patient.

U.S. Pat. No. 5,702,457, issued on Dec. 30, 1997 to Walsh et al., describes a humeral prosthesis including a shank having a metaphyseal part having a housing therein with a semi-spherical portion in which housing is introduced a sphere to which is secured a bearing surface hemispherical cap adapted to be received within the glenoid cavity of a shoulder. A securing element is provided which extends through the metaphyseal part of the shank for securing the sphere within the housing at a predetermined position with respect to the shank.

U.S. Pat. No. 5,725,597, issued on Mar. 10, 1998 to S. K. Hwang, describes an artificial hip joint having a construction capable of reducing abrasion of a polyethylene layer formed within the acetabulum cup when the head of the femur pivots in the acetabulum cup. The artificial acetabulum cup is implanted in the acetabulum of a user's pelvic bone and includes a hollow hemispherical member made of a metal. The polyethylene layer is formed on the inner surface of the hemispherical member. A femoral head holder is fixed to the femur. The femur head holder includes a spherical metal femur head pivotally held in the artificial acetabulum cup. A shaft is coupled at an upper end thereof to the femoral head and adapted to support the femoral head. A housing extends inclinedly through the greater trochanter of the femur and adapted to receive the shaft therein in such a manner that it rotates with respect to the shaft. Bearings are mounted between the shaft and the housing and are adapted to support axially and radial loads applied to the shaft at the femur head by the weight of the user.

It is an object of the present invention to provide a joint replacement system which minimizes the amount of invasive surgery.

It is another object of the present invention to provide an artificial joint system which minimizes rehabilitation and recovery time.

It is a further object of the present invention to provide a joint replacement system which minimizes the materials required for the joint replacement.

It is still another object of the present invention to provide an artificial joint system which simplifies surgical techniques for the installation of such a joint system.

It is another object of the present invention to provide a process in which joint replacements can be carried out on an outpatient basis.

It is still a further object of the present invention to provide an artificial joint system which is relatively inexpensive and reduces the cost of surgery.

It is another object of the present invention to provide an artificial joint system which can be installed with arthroscopic and fluoroscopic techniques.

The foregoing disclosure and description of the invention is illustrative and explanatory thereof. Various changes in the details of the illustrated construction may be made within the scope of the appended claims without departing from the true spirit of the invention.

SUMMARY OF THE INVENTION

The present invention is a joint replacement system which includes a first cup member having an interior lining material and forms a generally hemispherical cavity therein such that the interior lining material surrounds the hemispherical cavity, a ball member received within the hemispherical cavity so that the ball member is cantable within the cavity, a securing member connected to the first cup member for affixing the first cup member within a human bone adjacent to one component of the joint, and an affixation member interconnected to the ball member for affixing the ball member within another human bone adjacent another component of the joint. The ball member has a diameter of no more than one inch.

In the present invention, the securing member includes at least one screw having one end embedded in the first cup member. In the preferred embodiment of the present invention the human bone is a pelvic bone. The affixation member is a shaft which is affixed at one end to the ball member and extends into a femur bone. This affixation member further includes a nail extending through a portion of the femur bone so as to be engaged with the shaft distal the ball member. The ball member will extend outwardly of a surface of the femur head. A spacer ring may extend around the shaft so as to be interposed between the ball member and another surface of the femur head.

In an alternative embodiment of the present invention, a second cup member is provided so that the ball member has a portion received within the second cup member. The first cup member and the second cup member generally surround the ball member. The affixation member is connected to the second cup member so as to secure the second cup member and the ball member within another human bone. The affixation member includes at least one screw having an end embedded in the second cup member. The second cup member has an interior lining and has a generally hemispherical cavity therein. The interior lining generally surrounds the hemispherical cavity. The second ball member is received within the hemispherical cavity of the second cup member and is cantable within the second cup member. In another embodiment of the present invention, a rod has one end connected to the first ball member and an opposite end connected to the second ball member.

In a further embodiment of the present invention, a shaft has one end connected to the ball member. The affixation member will comprise a threaded surface formed on the shaft. The threaded surface engages another human bone adjacent to another component of the joint. The securing member includes at least one screw having an end embedded in the first cup member. The human bone is the femoral head of a human hip. The threaded surface engages the pelvic bone adjacent to the acetabulum area.

The present invention is further a method of forming an artificial human joint which comprises the steps of: (1) forming a first cup member having a hemispherical cavity of no more than one inch therein; (2) drilling a hole through two components of the human joint; (3) implanting the first cup member into one of the two components and into a portion of the drilled hole such that the hemispherical cavity faces the other component; (4) implanting a shaft having a ball member at one end into the other of the two components of the human joint and into a portion of the hole such that the ball member extends outwardly of the other of the components; and (5) engaging the ball member into the hemispherical cavity. In this method, a lining material is installed into the hemispherical cavity such that the lining material surrounds the hemispherical cavity.

The step of drilling in this method includes the steps of initially drilling a small hole through the two components of the human joint. A guide wire is fastened into the drilled hole such that the guide wire extends through and outwardly of the drilled hole. The guide wire receives a reaming device such that the reaming device reams a bore into a bone at the joint having a diameter suitable for allowing the first cup member to pass therethrough and for receiving the first cup member therein. After the bore has been suitably reamed, the guide wire can be removed from the drilled hole. The area between the shaft and the wall of the bore can be filled with a cementing material.

In the method of the present invention, the shaft is permanently affixed by attaching a surgical nail through a bone of one of the two components of the joint such that the nail engages the shaft so as to retain the shaft in a fixed position. The cup member is permanently affixed within the bones by placing at least one surgical screw through the other of the two components such that an end of the screw engages the first cup member so as to retain the cup in a fixed position.

DETAILED DESCRIPTION OF THE PRESENT INVENTION

Figures 1, 2:
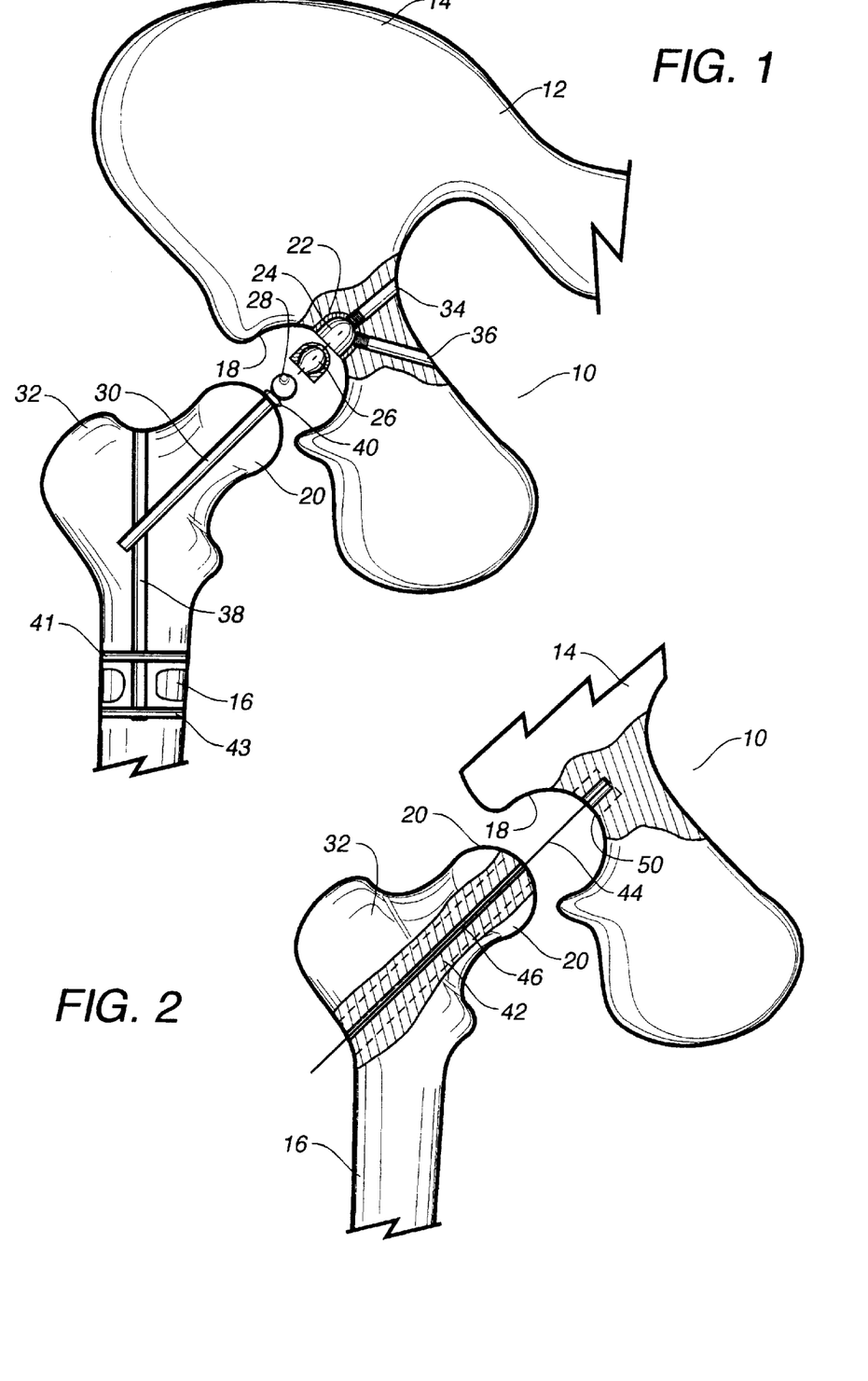
FIG. 1 is an exploded, partially cross-sectional view of the joint replacement system of the present invention.
FIG. 2 is an exploded, partially cross-sectional view showing the forming of the joint replacement system of the present invention.

Referring to FIG. 1, there is shown at 10 the joint replacement system in accordance with the preferred embodiment of the present invention. As shown in FIG. 1, the artificial joint system 10 is shown as applied to a human hip 12. The human hip 12 includes a pelvic bone 14 and a femur 16. The artificial joint system is, in particular, applied to the acetabulum area 18 of the pelvic bone 14 and to the femoral head 20 of the femur 16.

As can be seen in FIG. 1, a first cup member 22 is shown as implanted within the pelvic bone 14 adjacent to the acetabulum area 18. This first cup member 22 has a hemispherical cavity 24. An internal lining material 26 is shown, in an exploded view, as received within the interior cavity 24 of the first cup member 22. The cup member 22 should be of a rigid material, such as carbide steel, titanium, a cobalt chromium alloy, or other rigid non-biodegradable materials. The lining material 26, on the other hand, should be of a generally flexible material such as polyethylene, TEFLON (TM) or other non-biodegradable materials. It is important that the lining material 26 have a long life. The lining material 26 should be of a low-friction material so that movement of the hip joint is facilitated rather than restricted by the arrangement of the lining material 26. The lining material 26 can be placed within the hemispherical cavity 24 and sealed within the cavity by known means.

A ball member 28 is received within the hemispherical cavity 24 and within the lining material 26. The ball member 28 has a shaft 30 affixed to a surface thereof. Shaft 30 extends from ball 28 and into the femoral head 20 of the femur 16 and inwardly toward the greater trochanter area 32 of the femur 16. When the ball 28 is properly installed within the cup member 22, the femoral head 20 can suitably rotate within the acetabulum area 18. The ball member will have a diameter of no more than one inch.

It is important to be able to secure the cup member 22 in its proper position facing the acetabulum area 18 of the pelvic bone 14. As such, securing members 34 and 36 are provided so as to engage the cup member 22. It can be seen that the securing members 34 and 36 are surgical screws which are installed through the pelvic bone 14 so as to threadedly engage the cup member 22. Such surgical screws are known in the art. Typically, surgical screws 34 and 36 are self-tapping screws which can be inserted into the material of the first cup member 22 by rotating the ends of the screws 34 and 36. The exact position of the screws 34 and 36 relative to the first cup member 22 can be observed by fluoroscopy during the surgical procedure. Similarly, it is necessary to secure the shaft 30 within the femoral head 20 of the femur 16. As such, a surgical nail 38 can be installed so as to extend through the greater trochanter area 32 and into the femoral cavity. The nail 38 can be installed by known surgical techniques. The nail 38 will engage the shaft 30 at an area distal the ball member 28. Surgical screws 41 and 43 engage the distal end of nail 38. Surgical screws are secured into and through the femur 16 and are trapped through nail 38.

In the present invention, a spacing ring 40 is placed around the exterior of the shaft 30 as to be interposed between the ball member 28 and the surface of the femoral head 20. Spacer member 40 can be sized or provided in multiple numbers so as to provide proper spacing between the femoral head 20 and the interior surfaces of the acetabulum area 18.

When installed, the small size of the ball member 28 and the cup member 24 allows for proper rotatable and cantable movement of the femur 16 with respect to the pelvic bone 14. During the surgical procedure, a capsulectomy is performed so as to remove materials in the acetabulum area 18. It has been found that suitable support is provided between the bone structures of the pelvic bone 14 and the femoral head 20 to allow for a long life of the joint system 10. Unlike existing surgical procedures, there is no need to carry out the extensive tasks of reaming the acetabulum area 18 or the removal of the femoral head 20. The femoral head 20 will remain as is and in place with the ball member 28 suitably positioned thereon. The capsulectomy and the forming of the various holes and openings can be carried out thorugh fluoroscopic and orthroscopic procedures.

FIG. 2 shows the initial technique for the installation of the system 10 of the present invention. Initially, a small hole is drilled through the greater trocanter area 32 and through the femoral head 20. This small hole will be drilled so as to extend through the femoral head 20 and into the acetabulum area 18 of the pelvic bone 14. This small hole can be drilled by existing surgical techniques. After the small hole has been drilled, a guide wire 44 is inserted through the small hole formed in the pelvic bone 14 and through the small hole 46 formed in the femur 16. This guide wire 44 can be anchored by known surgical techniques.

Once the guide wire 44 is in a suitable position, a reaming devices can be attached to the guide wire 44. Initially, a large diameter reaming device is provided so as to form a bore 42 extending therealong. This bore 42 is shown in broken line fashion. The diameter of the bore should be of a suitable diameter to accommodate the first cup member 22. As such, this bore 42 will have a diameter of no more htan one inch. The bore 42 which is formed over the existing hole 46 will also be suitable for the receipt of shaft 30 therein. The guide wire 44 can remain in place so as to allow for the installation the first cup member 22 and of the shaft 30 and its associated ball member 28. Alternatively, if possible, the guide wire 44 can be removed so that the shaft 30 and its associated ball member 28 (and possible spacer rings 40) can be placed within the formed bore in the femur 16. The guide wire can also remain in place so that the first cup member 22 can be properly positioned adjacent to the surface of the acetabulum area 18. When these components are properly placed, the screws 34 and 38 can be actuated so as to secure the first cup member 22 in place. Similarly, the nail 38 can be inserted through the femur 16 so as to secure the shaft member 30 in place. The shaft can be cemented in place within the bore 42. The femoral head 20 of the femur 16 can then be pushed such that the ball member 28 engages the interior cavity 24 of the first cup member 22. Surgical closure of any incisions or surgical openings can then be carried out in a known manner.

Figure 3:
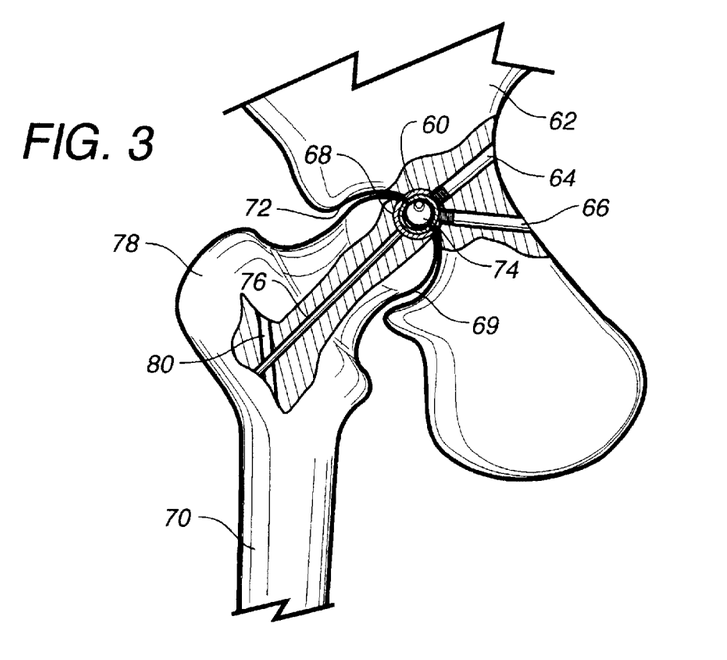
FIG. 3 is a partially cross-sectional view of a first alternative embodiment of the joint replacement system of the present invention.

FIG. 3 shows an alternative embodiment of the present invention. As can be seen in FIG. 3, a cup member 60 is inserted into the pelvic bone 62 in the manner described herein previously. Screws 64 and 66 are installed through the pelvic bone 62 so as to secure the cup member 60 in its proper position. Another cup member 68 is placed into the femoral head 69 of the femur 70. The cup member 68 has an interior lining surrounding the hemispherical cavity of cup member 68. The opening which is used to receive the second cup member 68 can be formed by the techniques described herein previously. It is simply necessary that a larger hole be formed adjacent and into the femoral head 69 at the area adjacent to the acetabulum area 72 of the pelvic bone 62. As can be seen, a ball member 74 is received within the first cup member 60 and within the second cup member 68. In this embodiment of the present invention, the surface of the femoral head 69 will be in close contact with the surface of the acetabulum area 72. The second cup member 68 is secured to a shaft 76. Shaft 76 extends into the greater trochanter area 78 of the femur 70. A nail 80 will extend through the femur 70 transverse to the shaft 76 of the second cup member 68 so as to secure the shaft 76 and the second cup member 68 in their desired positions.

Figure 4:
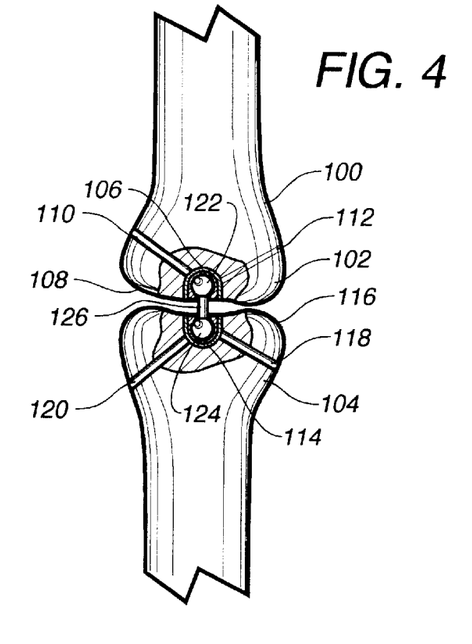
FIG. 4 is a frontal partially cross-sectional view of a second alternative embodiment of the present invention as used in association with a human knee.

FIG. 4 shows the installation of the present invention, in another embodiment, with a knee joint 100. The knee joint 100 has upper component 102 and lower component 104. As can be seen, a first cup member 106 is installed on the end surface 108 of the upper component 102. Screws 110 and 112 are used so as to secure the first cup member 106 in its desired position. Similarly, a second cup member 114 is installed within the top surface 116 of the second component 104 of knee 100. The second cup member 114 is secured in place through the use of surgical screws 118 and 120.

Unlike the previous embodiments of the present invention, the embodiment shown in FIG. 4 employs a first ball member 122 and a second ball member 124. A rod 126 connects the first ball member 122 to the second ball member 124. The first ball member 122 is received within the first cup member 106. The second ball member 124 is received within the second cup member 114. As such, proper movement is achieved, in a normal fashion, between the upper component 102 and the lower component 104 of knee 100.

Figure 5:
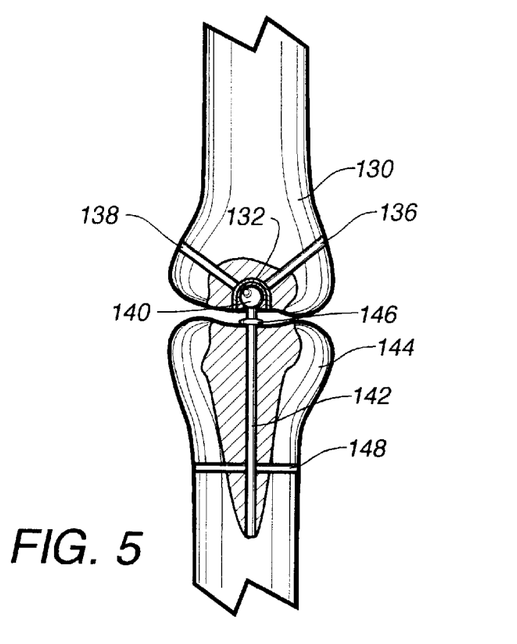
FIG. 5 is a frontal partially cross-sectional view of the preferred embodiment of the present invention as used in association with a human knee.

FIG. 5 shows another form of the present invention as applied to knee 130. As can be seen in FIG. 5, a first cup member 132 is formed in the upper component 134 of knee 130. Screws 136 and 138 are used so as to secure the first cup member 132 in a desired position. A ball member 140 is received within the first cup member 132. The ball member 140 has a shaft 142 affixed thereto and extending into the lower component 144 of knee 130. A spacer ring 146 is used to facilitate the proper spacing between the upper component 132 and the lower component 144 of knee 130. A nail 148 is used so as to secure the shaft 142 in its desired position. As can be seen, the present invention can be employed so as to establish the proper jointed relationship between the knee components.

Figure 6:
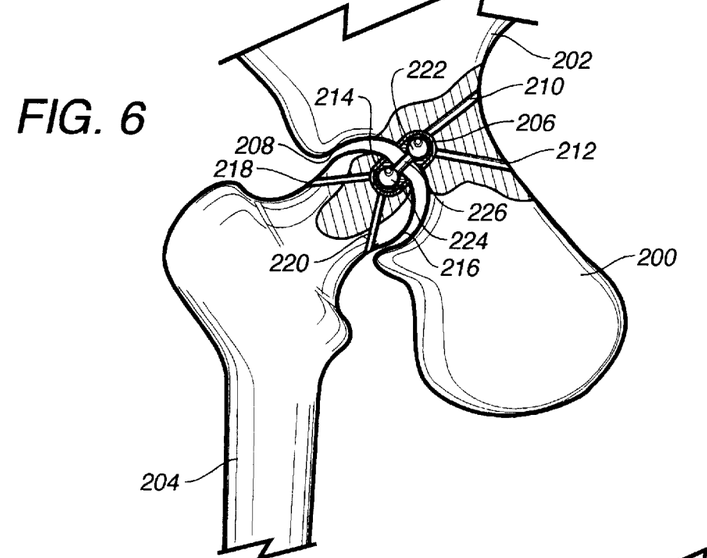
FIG. 6 is a partially cross-sectional view showing the second alternative system of FIG. 4 as used in association with a human hip.

FIG. 6 shows the embodiment illustrated in FIG. 4 as applied to a hip joint 200. Hip joint 200 includes pelvic bone 202 and femur 204. The first cup member 206 is installed adjacent to the acetabulum area 208 of the pelvic bone 202. Screws 210 and 212 are employed so as to secure the first cup member 206 in its desired position adjacent to the acetabulum area 208. A second cup member 214 is placed on the femoral head 216 of femur 214. Screws 218 and 220 are used so as to secure this second cup member 214 in its desired position. Screws 218 and 220 can be installed in standard surgical procedures.

In the embodiment of FIG. 6, a first ball member 222 is received within the hemispherical cavity of the first cup member 206. A second ball member 224 is received within the hemispherical cavity of the second cup member 214. Rod 226 will extend between the first ball member 222 and the second ball member 224. Rod 226 will have a suitable length so as to establish proper spacing between the femoral head 216 of femur 204 and the acetabulum area 208 of the pelvic bone 202.

Figure 7:
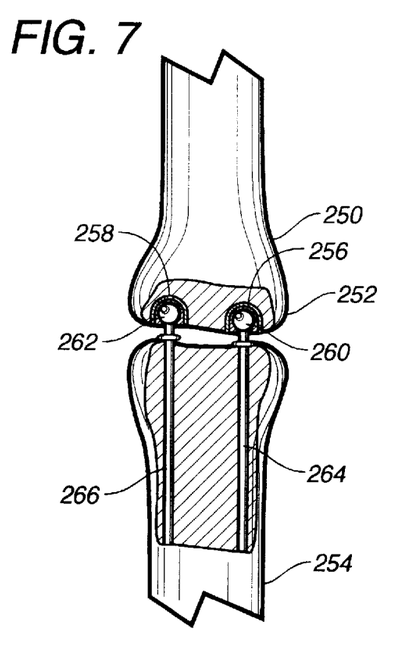
FIG. 7 is a third alternative embodiment of the present invention showing a dual system as used with a human knee joint.

FIG. 7 shows a knee joint 250 with an upper component 252 and a lower component 254. As can be seen, a dual system of sockets 256 and 258 with ball members 260 and 262, respectively, are employed. Each of the ball members 260 and 262 have shafts 264 and 266, respectively, attached thereto. The shafts 264 and 266 will extend into the second component 254 of the knee 250. This arrangement is provided so as to give additional rigidity and structural support to the knee joint 250. As described herein previously, suitable surgical screws and nails can be installed to affix the cup members 256 and 258, along with the shafts 264 and 266, in their proper position relative to the components of knee 250.

Figure 8:
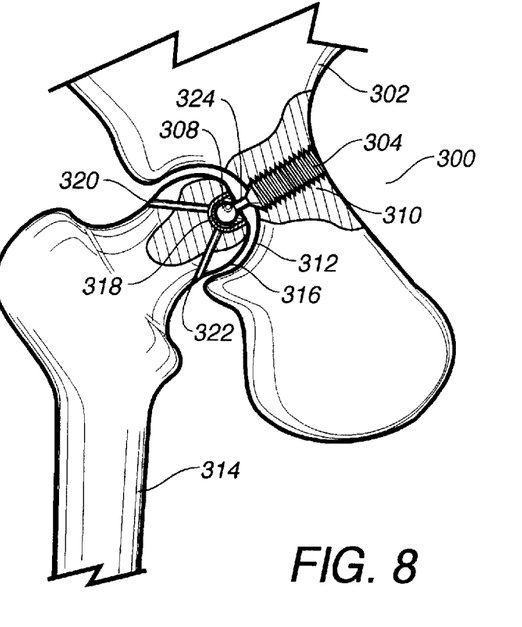
FIG. 8 is a fourth alternative embodiment of the present invention showing the joint replacement system of the present invention as used with a human hip.

FIG. 8 shows another embodiment 300 of the artificial joint system of the present invention. In the embodiment 300, as shown in FIG. 8, the pelvic bone 302 receives a threaded shaft 304 attached to ball member 308. The shaft 304 is threaded so that it can properly engage a hole 310 formed in the pelvic bone 302 adjacent to the acetabulum area 312. The threads on the shaft 304 are suitable for engaging the surfaces of hole 310 such that the shaft 304 is rigidly retained in position. The femur 314 has a femoral head 316. A first cup member 318 is affixed within the femoral head 316 of the femur 314. In this arrangement, the ball 308 is received within this first cup member 318. Screws 320 and 322 are installed into the femoral head 316 so as to retain the cup member 318 in its desired position. A rod 324 is provided so as to serve to space the distance between the ball member 308 and the threaded shaft 304 so as to properly space the distance between the acetabulum area 312 of the pelvic bone 302 and the femoral head 316 of the femur 314.

Figure 9:
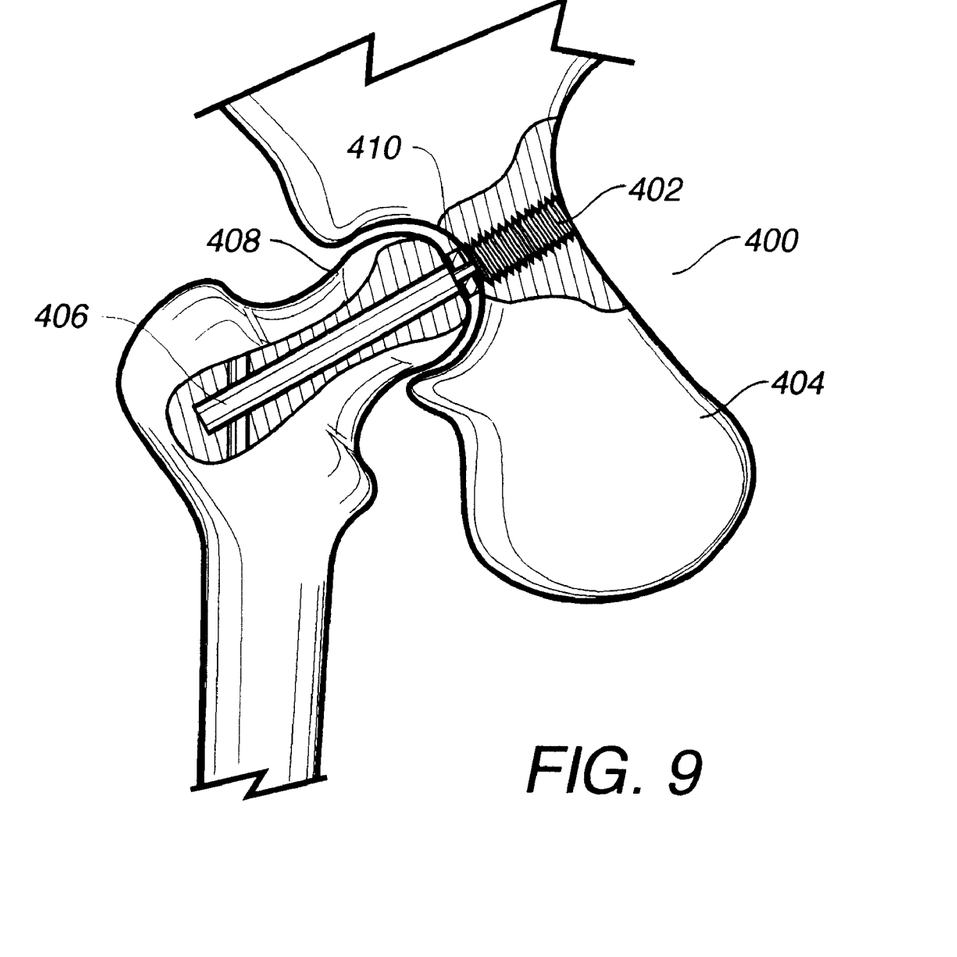
FIG. 9 is a fifth alternative embodiment of the present invention showing a ring and bearing system for the joint replacement system.

FIG. 9 shows another embodiment 400 of the present invention. In this form of the present invention, a first shaft 402 is secured within the pelvic bone 404 in accordance with any of the various techniques described herein previous. Similarly, another shaft 406 is installed so as to extending through the femoral head 408. An axle-and-ring system 410 connects the first shaft 402 to the other shaft 406. The axle-and-ring system 410 is initially formed such that the first shaft 402 is connected to the second shaft 406 prior to installation. The axle-and-ring system allows for proper joint-like movement between the joint components.

Importantly, in the present invention, the installation of the artificial joint avoids many of the complicated and dangerous proceedings associated with common hip, knee and elbow replacement surgeries. In the present invention, it is not necessary to remove the femoral head of the femur. Additionally, it is not necessary to ream the acetabulum area completely of the pelvic bone. As a result, only a minimal incision is required to carry out the installation of the hip joint of the present invention. Incisions are only required so as to carry out the necessary reaming for the installation of the various shaft and cup components of the present invention. Surgical screws and nails are installed in a simple surgical and non-invasive manner. In theory, the entire process of installing the artificial joint system of the present invention can be carried out through arthroscopic and fluorosopic guide procedures. Ideally, only a very minimal hospital stay is required for recovery and very minimal rehabilitation efforts will be required in order to restore full movement of the joint.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A replacement system for a joint comprising:

a first cup member having an interior lining material, said first cup member having a generally hemispherical cavity therein, said interior fining material generally surrounding said hemispherical cavity;

a ball member received within said hemispherical cavity, said ball member being cantable within said cavity;

a securing means connected to said first cup member for affixing said first cup member within a human bone adjacent one component of the joint;

an affixation means interconnected to said ball member for affixing said ball member within another human bone adjacent another component of the joint; and a second cup member having an interior lining said second cup member forming a generally hemispherical cavity therein said interior lining material surrounding said hemispherical cavity of said second cup member, said ball member having a portion received within said second cup member, said first cup member and said second cup member generally surrounding said ball member, said affixation means connected to said second cup member so as to secure said second cup member and said ball member within another human bone.

2. The system of claim 1, said ball having a diameter of no more than one inch.

3. The system of claim 1, said securing means being at least one screw having one end embedded in said first cup member.

4. The system of claim 3, said affixation means being a shaft affixed at one end to said ball member, said affixation means further comprising a nail engaged with said shaft distal said ball member.

5. The system of claim 1, further comprising:

a spacer ring extending around said shaft.

6. The system of claim 1, said affixation means comprising at least one screw having an end embedded in said second cup member.

7. The system of claim 1, further comprising:

a shaft having one end connected to said ball member, said affixation means comprising a threaded surface formed on said shaft, said threaded surface for engaging said another human bone adjacent to said another component of the joint.

8. The system of claim 7, said securing means comprising at least one screw having an end embedded in said first cup member.

9. A replacement system for a joint comprising:

a first cup member having an interior lining material, said first cup member having a generally hemispherical cavity therein, said interior lining material generally surrounding said hemispherical cavity;

a ball member received within said hemispherical cavity, said ball member being cantable within said cavity;

a securing means connected to said fist cup member for affixing said first cup member within a human bone adjacent one component of the joint;

an affixation means interconnected to said ball member for affixing said ball member within another human bone adjacent another component of the joint;

a second cup member having an interior lining, said second cup member forming a generally hemispherical cavity therein, said interior lining generally surrounding said hemispherical cavity in said second cup member;

a second ball member received within said hemispherical cavity of said second cup member, said second ball member being cantable within said second cup member; and a rod having one end connected to said first ball member and an opposite end connected to said second ball member.

10. A method of forming an artificial human joint comprising:

forming a first cup member having a hemispherical cavity therein, said hemispherical cavity having a diameter of not more than one inch;

drilling a hole through two components of the human joint, said step of drilling comprising the steps of:
　fastening a guide wire into the drilled hole, said guide wire extending through and outwardly of said drilled hole;
　reaming a bore along said guide wire into a bone at the joint having a diameter suitable for receiving said first cup member;
　removing said guide wire from said drilled hole; and cementing areas between exterior surfaces of said shaft and an interior wall of the bore;

implanting said first cup member into one of the two components of the human joint and into a portion of said hole, said hemispherical cavity facing the other of said two components;

implanting a shaft having a ball member at one end into the other of said two components and into another portion of the drilled hole such that said ball faces said hemispherical cavity; and engaging said ball member into said hemispherical cavity.

11. The method of claim 10 said step of forming comprising:

installing a lining material into said hemispherical cavity such that said lining material surrounds said hemispherical cavity.

12. The method of claim 10, said step of implanting comprising:

affixing a nail through a bone of said one of the two components of the joint, said nail engaging said shaft so as to retain said shaft in a fixed position.

13. The method of claim 10, said step of implanting further comprising:

placing a spacer ring around said shaft adjacent to said ball, said spacer ring being interposed between said ball and an outer surface of said one of the two components.

14. The method of claim 10, further comprising the step of:

placing at least one screw through said other of the two components such that an end of the screw engages said first cup member so as to retain said first cup member in a fixed position.

15. The method of claim 10, the human joint being a hip joint having a pelvic bone with an acetabulum area and a femur with a femoral head, said shaft extending into said femur such that said ball resides on an existing surface of the femoral head, said first cup member being implanted into said acetabulum area of said pelvic bone.

16. The method of claim 10, the human joint being a hip joint having a pelvic bone with an acetabulum area and a femur with a femoral head, said first cup member being implanted into a surface of the femoral head, said shaft extending into said acetabulum area of said pelvic bone.

17. The method of claim 16, said shaft being externally threaded, said step of implanting comprising:

threadedly engaging said shaft with an internally threaded area in said pelvic bone at said acetabulum area.

* * * * *